United States Patent
Fridman

(10) Patent No.: US 11,432,768 B2
(45) Date of Patent: *Sep. 6, 2022

(54) DEVICE AND SYSTEM FOR SENSING MEDICALLY RELEVANT INFORMATION FROM THE MOUTH

(71) Applicant: MULTISENSOR DIAGNOSTICS, LLC, Baltimore, MD (US)

(72) Inventor: Gene Yevgeny Fridman, Baltimore, MD (US)

(73) Assignee: Aidar Health, Inc., Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/859,207

(22) Filed: Apr. 27, 2020

(65) Prior Publication Data
US 2020/0253551 A1 Aug. 13, 2020

Related U.S. Application Data

(63) Continuation of application No. 13/819,399, filed as application No. PCT/US2011/049302 on Aug. 26, 2011, now Pat. No. 10,674,960.
(Continued)

(51) Int. Cl.
*A61B 5/00* (2006.01)
*A61B 5/11* (2006.01)
(Continued)

(52) U.S. Cl.
CPC ............... *A61B 5/682* (2013.01); *A61B 5/01* (2013.01); *A61B 5/02055* (2013.01); *A61B 5/11* (2013.01);
(Continued)

(58) Field of Classification Search
CPC ......... A61B 5/682; A61B 5/318; A61B 5/369; A61B 5/389; A61B 5/01; A61B 5/02055;
(Continued)

(56) References Cited

U.S. PATENT DOCUMENTS

| 4,510,941 A | 4/1985 | Semrow et al. |
| 6,379,311 B1 | 4/2002 | Gaumond et al. |

(Continued)

OTHER PUBLICATIONS

Koon, Y., et al., "Non-constrained Blood Pressure Monitoring Using E(pG and PPG for Personal Healthcare," Journal of Medical Systems, vol. 33, No. 4, pp. 261-266, Aug. 2009.
(Continued)

*Primary Examiner* — Gary Jackson
*Assistant Examiner* — Sebastian X Lukjan
(74) *Attorney, Agent, or Firm* — Murtha Cullina LLP; Anthony P. Gangemi

(57) ABSTRACT

An intraoral multisensor device includes a mouthpiece, a plurality of sensors at least one of attached to or integrated with the mouthpiece, and a data communications unit configured to receive signals from the plurality of sensors. The mouthpiece has a form to permit stable arrangement at least partially within a person's mouth such that it can remain for hands-free sensing of a plurality of biological parameters. Also, an intraoral multisensor system includes an intraoral multisensor device and a data processing device adapted to communicate with the intraoral multisensor device.

26 Claims, 9 Drawing Sheets

Related U.S. Application Data

(60) Provisional application No. 61/377,609, filed on Aug. 27, 2010.

(51) Int. Cl.

| | | |
|---|---|---|
| *A61C 5/90* | (2017.01) |
| *A61B 5/318* | (2021.01) |
| *A61B 5/369* | (2021.01) |
| *A61B 5/389* | (2021.01) |
| *A61B 5/01* | (2006.01) |
| *A61B 5/0205* | (2006.01) |
| *A61B 5/145* | (2006.01) |
| *A61B 5/22* | (2006.01) |
| *A61B 5/021* | (2006.01) |
| *A61B 5/1455* | (2006.01) |
| *A61B 7/00* | (2006.01) |
| *A61B 5/08* | (2006.01) |

(52) U.S. Cl.
CPC .......... *A61B 5/14542* (2013.01); *A61B 5/228* (2013.01); *A61B 5/318* (2021.01); *A61B 5/369* (2021.01); *A61B 5/389* (2021.01); *A61B 5/4277* (2013.01); *A61C 5/90* (2017.02); *A61B 5/021* (2013.01); *A61B 5/082* (2013.01); *A61B 5/0816* (2013.01); *A61B 5/14507* (2013.01); *A61B 5/14532* (2013.01); *A61B 5/14551* (2013.01); *A61B 7/003* (2013.01); *A61B 2562/06* (2013.01)

(58) Field of Classification Search
CPC ... A61B 5/14542; A61B 5/228; A61B 5/4277; A61B 5/11; A61B 5/021; A61B 5/14532; A61B 5/14551; A61B 2562/06; A61B 7/003; A61B 5/14507; A61B 5/0816; A61B 5/082; A61C 5/90
See application file for complete search history.

(56) References Cited

U.S. PATENT DOCUMENTS

| | | |
|---|---|---|
| 7,204,250 B1 | 4/2007 | Burton |
| 7,407,484 B2 | 8/2008 | Korman |
| 7,481,772 B2 | 1/2009 | Banet |
| 10,076,268 B1 | 9/2018 | Dietrich et al. |
| 10,674,960 B2 * | 6/2020 | Fridman ................ A61B 5/389 |
| 2003/0040679 A1 | 2/2003 | Weber et al. |
| 2004/0181166 A1 | 9/2004 | Williford et al. |
| 2004/0186390 A1 | 9/2004 | Ross et al. |
| 2006/0276718 A1 | 12/2006 | Madaus et al. |
| 2007/0106138 A1 | 5/2007 | Beiski et al. |
| 2007/0277823 A1 | 12/2007 | Al-Ali et al. |
| 2008/0269579 A1 | 10/2008 | Schiebler |
| 2009/0069642 A1 | 3/2009 | Gao et al. |
| 2009/0221884 A1 | 9/2009 | Ryan |
| 2010/0085067 A1 | 4/2010 | Gabriel et al. |

OTHER PUBLICATIONS

Lima, D., et al., "Saliva: reflection of the body," International Journal of Infectious Diseases, vol. 14, No. 3, pp. e184-e188, Mar. 2010.

Scott, D., et al., "Diabetes-related molecular signatures in infrared spectra of human saliva," Diabetology & Metabolic Syndrome, vol. 2, p. 48, 2010.

DiRienzo, M., et al., "Textile Technology for the Vital Signs Monitoring in Telemedicine and Extreme Environments," IEEE Transactions on Information Technology in Biomedicine, vol. 14, No. 3, pp. 711-717, May 2010.

Caduff, A., et al., "Characteristics of a multisensor system for non invasive glucose monitoring with external validation and prospective evaluation," Biosensors and Bioelectronics, vol. 26 (2011), pp. 3794-3800.

Reisner, A., et al., "Utility of the Photoplethysmogram in Circulatory Monitoring," Anesthesiology, vol. 108, No. 5, pp. 950-958, May 2008.

Definition of Integrated. Merriam-Webster Dictionary, retrieved on Aug. 19, 2017; retrieved from the Internet: http://www.merriam-webster.com/dictionary/integrated.

Definition of Couple. Merriam-Webster Dictionary, retrieved on Oct. 12, 2016; retrieved from the Internet: http://www.merriam-webster.com/dictionary/couple.

* cited by examiner

DEVICE AND SYSTEM FOR SENSING MEDICALLY RELEVANT INFORMATION FROM THE MOUTH

CROSS-REFERENCE OF RELATED APPLICATION

This application is a continuation of U.S. Utility patent application Ser. No. 13/819,399, filed Feb. 27, 2013, which is a 35 U.S.C. § 371 U.S. national entry of International Application PCT/2011/049302 having an international filing date of Aug. 26, 2011, which claims the benefit of U.S. Provisional Application No. 61/377,609 filed Aug. 27, 2010, the entire contents of which are hereby incorporated by reference.

BACKGROUND

1. Field of Invention

The field of the currently claimed embodiments of this invention relates to devices and systems for sensing medically relevant data, and more particularly to devices and systems for sensing medically relevant data from the mouth.

2. Discussion of Related Art

Recently, efforts have been directed towards obtaining medical measurements remotely for the use of home care medicine as well as for remote diagnosis in poor countries where immediate access to expert medical care often is not available. A goal of telemedicine is to provide more efficient medical care and deliver it to more people. Much of the effort devoted to research and development of telemedicine has been in security, network, and information accessibility. Less effort has been directed toward obtaining objective measurements from the body that could be easily integrated into a model. There thus remains a need for improved devices and systems for sensing medically relevant data that can be used in telemedicine and/or other applications.

SUMMARY

An intraoral multisensor device according to an embodiment of the current invention includes a mouthpiece, a plurality of sensors at least one of attached to or integrated with the mouthpiece, and a data communications unit configured to receive signals from the plurality of sensors. The mouthpiece has a form to permit stable arrangement at least partially within a person's mouth such that it can remain for hands-free sensing of a plurality of biological parameters.

An intraoral multisensor system according to an embodiment of the current invention includes an intraoral multi sensor device and a data processing device adapted to communicate with the intraoral multisensor device. The intraoral multisensor device includes a mouthpiece, a plurality of sensors at least one of attached to or integrated with the mouthpiece, and a data communications unit configured to receive signals from the plurality of sensors. The mouthpiece has a form to permit stable arrangement at least partially within a person's mouth such that it can remain for hands-free sensing of a plurality of biological parameters and to provide data for the plurality of biological parameters to the data processing device.

BRIEF DESCRIPTION OF THE DRAWINGS

Further objectives and advantages will become apparent from a consideration of the description, drawings, and examples.

DETAILED DESCRIPTION

Figure 1A:
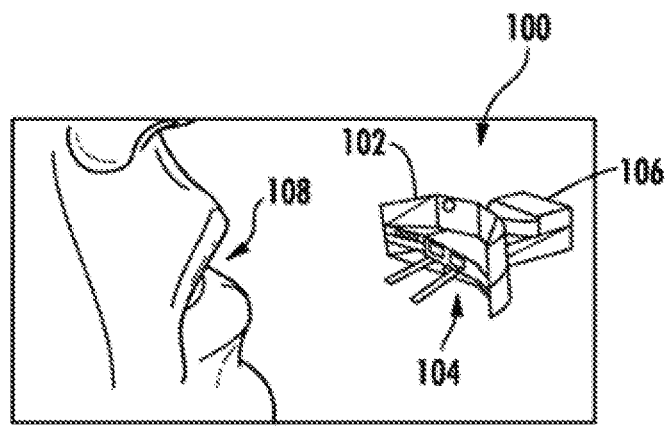
FIGS. 1A-1C are schematic illustrations of an intraoral multisensor device according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Some aspects of the current invention can provide devices and systems to reduce cost, discomfort, and time associated with patient diagnosis and disease monitoring in a wide variety of medical and home health care applications. A device according to some embodiments of the current invention can accumulate many biomedical measurements simultaneously and non-invasively from one location on the body and export those data via wireless technology to a CPU, or any suitable data processing system, for integration and analysis. Embodiments of the current invention focus on the oral cavity as a suitable single location on the body for providing a large amount of biomedical data because of the proximity of blood vessels and breathing patterns for obtaining biophysical measurements and the availability of oral fluids and respiratory gasses for biochemical analysis. In addition, the skeletal and muscular structure of the mouth allows for easy positioning of a device for obtaining these measurements.

A non-invasive, inexpensive, robust, and wireless system according to some embodiments of the current invention is designed to collect vital signs and other biomedical signals from the mouth of a patient. An intraoral multisensory device according to some embodiments of the current invention fits around the teeth of a patient in a way that is similar to a mouth guard often used by athletes, or a retainer used in orthodontics. The intraoral multisensory device can have a variety of sensors to collect measurements from the patient's gums, teeth, saliva, and tongue, such as vital signs, respiratory measures, blood oxygen level, head motion, and saliva chemistry, for example. These measurements can be sent wirelessly to a PDA, a smartphone, a PC and/or other systems according to the particular application to process and/or display medically relevant information. Some embodiments of the current invention can include software on the receiving end that records, plots, and analyzes the data in real time, correlates the measurements to symptoms, and can optionally suggest treatment options.

Devices and systems according to some embodiments of the current invention can be useful in large scale emergency situations, such as fire, battlefield, and natural disasters, for example, where fast collection of vital signs from a number of patients will assist in making triage decisions. Additionally, devices and systems according to some embodiments of the current invention can be used effectively to make collection of information more comfortable for the geriatric patient population and for patients who are suffering from long-term, but not debilitating illnesses that require these measurements to be taken periodically at home, where having more extensive biomedical monitoring equipment is prohibitively expensive or impractical. A similar argument can be made for using this device to supplement health monitoring in the poorer parts of the world, where access to medical equipment and personnel is limited. Further use of this device can be for monitoring a patient's symptoms associated with sleep disorders by collecting the patient's movement data throughout the night. According to some embodiments of the current invention, soldiers, firemen, astronauts, and athletes, for example, can wear the device during dangerous or stressful situations to provide remote health monitoring in real time. In further embodiments of the current invention, real-time detection of illicit drug use can be included for use by law enforcement and road-side testing.

Figure 1B:
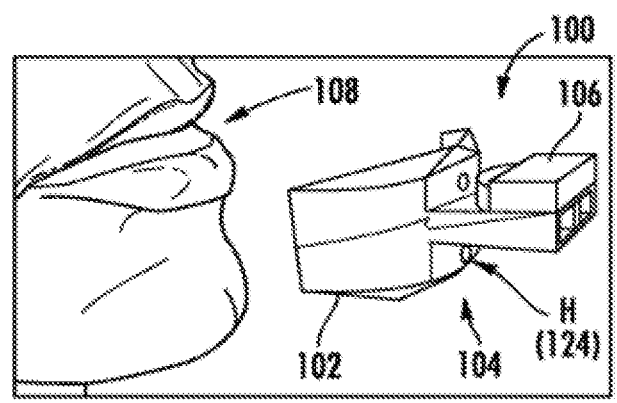
Figure 1C:
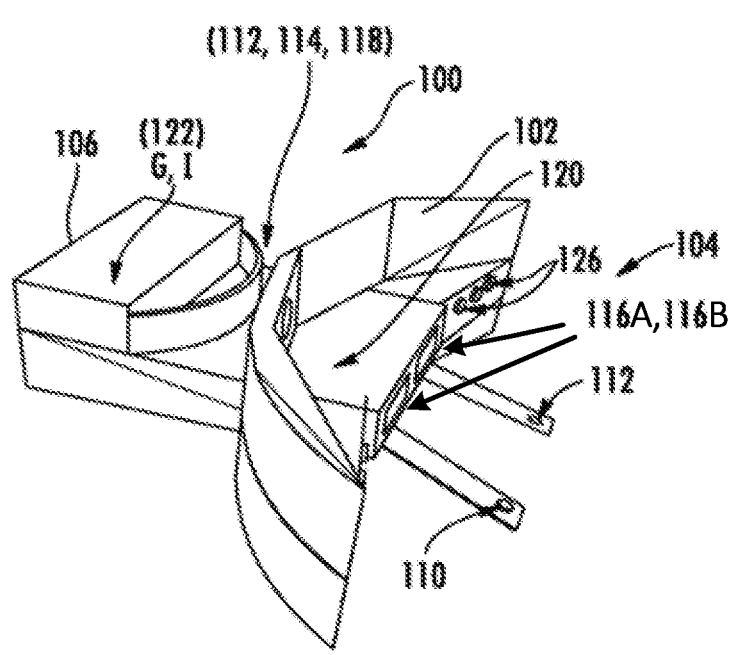

FIGS. 1A-1C show three different perspective views of an intraoral multisensor device 100 according to an embodiment of the current invention. The intraoral multisensor device 100 includes a mouthpiece 102, a plurality of sensors 104 at least one of attached to or integrated with the mouthpiece 102, and a data communications unit 106 configured to receive signals from the plurality of sensors 104. The mouthpiece 102 has a form to permit stable arrangement at least partially within a person's mouth 108 such that it can remain for hands-free sensing of a plurality of biological parameters.

In some embodiments of the current invention, the data communications unit 106 can include a wireless transmitter that is configured to transmit data from the plurality of sensors 104 to a processing device (not shown in FIGS. 1A-1C). The wireless transmitter can be, but is not limited to, a Bluetooth wireless transmitter. In some embodiments of the current invention, the data communications unit 106 can additionally, or alternatively, include a data storage component that is adapted to be at least one of removed or accessed to retrieve stored data. For example, the data storage component can be, but is not limited to, semiconductor memory components, such a flash memory, etc. that can be removed and/or accessed by plugging into the intraoral multisensor device 100. In some embodiments of the current invention, the data communications unit 106 can additionally, or alternatively, include a user interface to at least one of output information directly to a user or receive user input information. For example, the user interface can include an LCD display, or other suitable display device for the output of information directly to a user, or can include a touch screen display for both output and input of information. However, the broad concepts of the current invention are not limited to these examples. Other embodiments can include a wide range of alternative input and output interfaces for direct access by a user including audio output and tongue position sensor for input interface.

Figure 2:
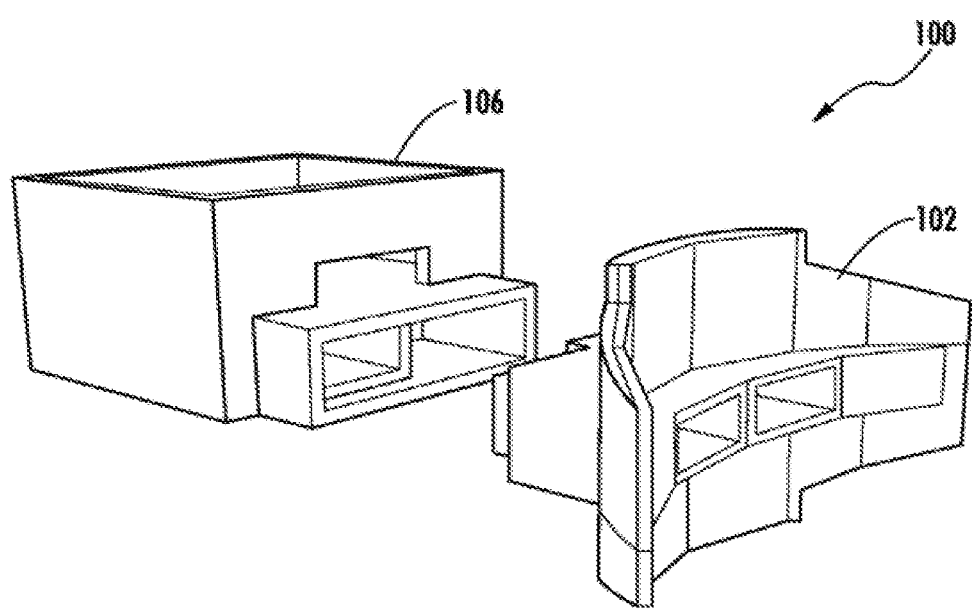
FIG. 2 is a schematic illustration of an intraoral multi-sensor device according to an embodiment of the current invention that has a removable mouthpiece.

In some embodiments of the intraoral multisensor device 100, the mouthpiece 102 and the data communications unit 106 are attachable together for use and detachable after use as is illustrated schematically in FIG. 2. This can allow the mouthpiece to be either cleaned for reuse, or discarded and replaced with a new or cleaned mouthpiece. In some embodiments, the communications unit 106 will contain the more expensive electronics and/or sensors which can thus be easily reused.

In some embodiments of the intraoral multisensor device 100, the plurality of sensors 104 can include a plurality of vital signs sensors. The plurality of vitals signs sensors can include at least two sensors selected from a temperature sensor 110, a blood pressure sensor 112, a pulse rate sensor 114, a breath condensate analyzer, a breath pattern analyzer, an electromyography (EMG) electrodes, an electroencephalography (EEG) electrodes, and an electrocardiography (ECG) electrodes, and a respiratory rate sensor. The breath pattern analyzer can include a broadband microphone or set of microphones that can sense a broad range of audio frequencies including those outside of human audio sensitivity. The analysis would use the data from these microphones to further determine the pathological breathing sounds and patterns. Each of the EMG, EEG, and/or ECG sensors can be metal electrodes that can be positioned on the intraoral component.

In some embodiments of the intraoral multisensor device 100, the plurality of sensors 104 can include at least one of a vital signs sensor, a blood oxygen level sensor 118, a bite pressure sensor 120, a head motion sensor 122, a saliva analysis sensor 124 or a tongue position sensor 126.

Figure 3:
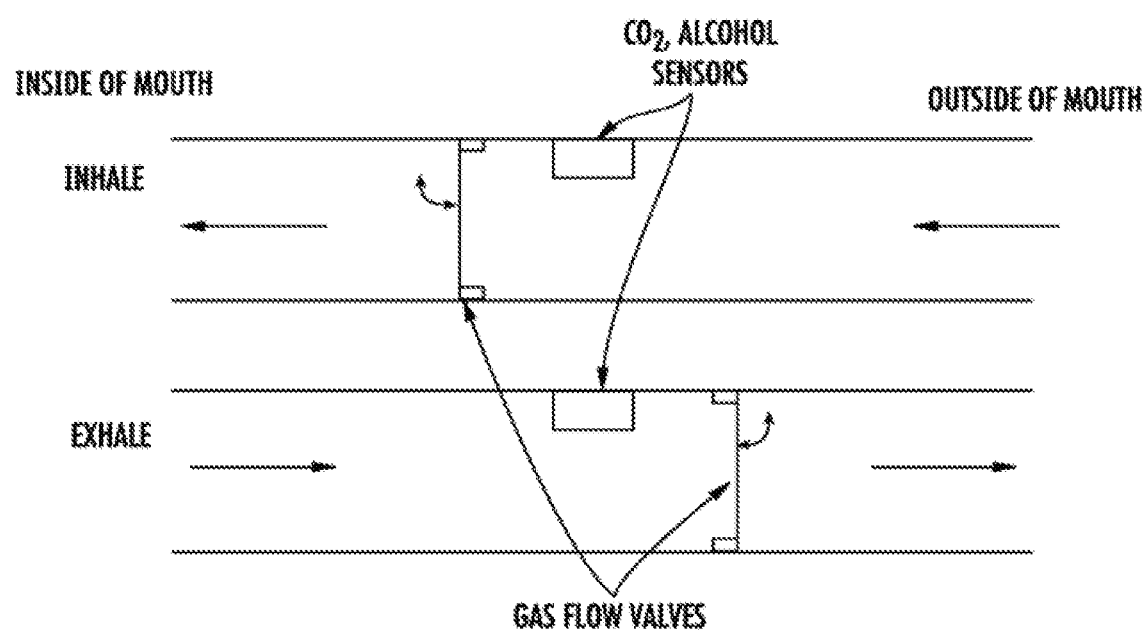
FIG. 3 is a schematic illustration of a pair of air channels and sensors for an intraoral multisensor device according to an embodiment of the current invention.
Figure 4A:
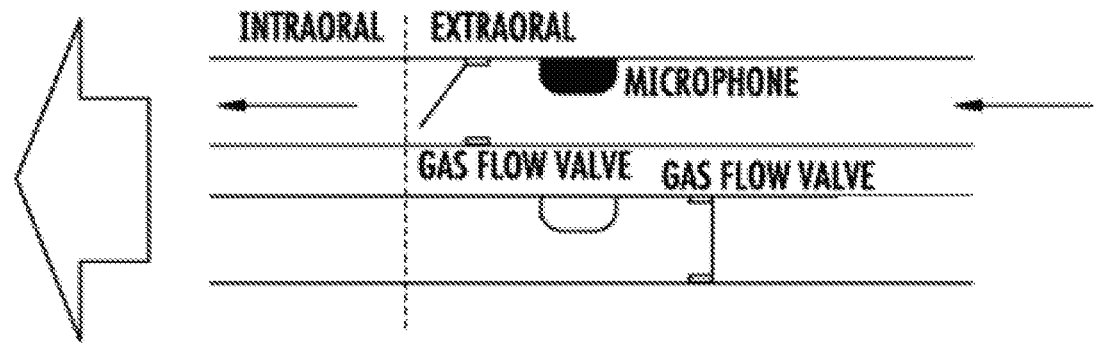
FIGS. 4A and 4B are schematic illustrations of a pair of air channels and sensors for an intraoral multisensor device according to another embodiment of the current invention.
Figure 4B:
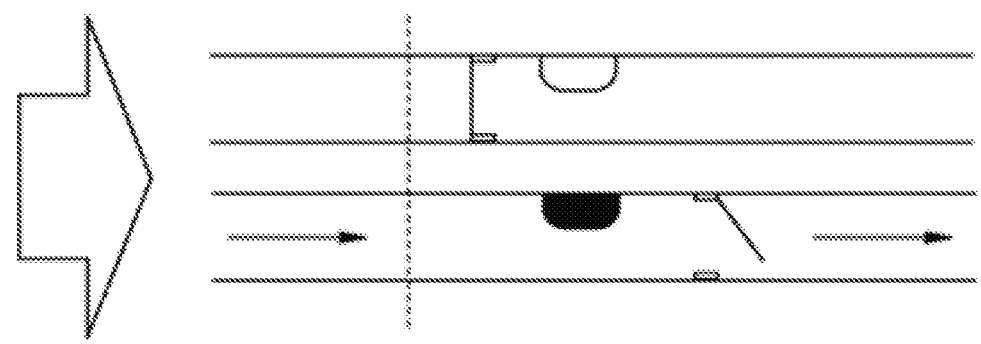

Referring now to FIG. 1C, the intraoral multisensor device 100 includes two sensor chambers 116A and 116B for measuring respiratory rate, metabolic activity, and/or breath alcohol content, for example. FIG. 3 is a schematic illustration representing the two sensor chambers, e.g., 116A and 116B from FIG. 1C. One of the two chambers is used for inhalation and the second for exhalation part of the breathing cycle. FIG. 3 is an embodiment that includes sensors, such as CO2 sensors. In addition, or alternatively, microphones, for example, can be included to measure breathing patterns and breathing rate as is illustrated in FIGS. 4A and 4B. For example, the frequency and duration of inhaling and exhaling can be measured according to some embodiments. In other embodiments, additional information may be obtained from the signals from the microphone, such as flow volume, etc. The air flow control and breathing measurement can be accomplished by oppositely oriented valves, one in each chamber. The valves can generate controlled back-pressure to allow accurate measurement of lung pressure. Both chambers in FIG. 3 contain CO2 and alcohol sensors. The valves prevent contamination of the gas measurement from external air in the exhalation chamber and from the mouth air in the inhalation chamber. Subtracting the measured concentration of the gas in the inhaled from the exhaled chamber allows the comparison between the two for an accurate measurement of the gas concentrations produced by the body. Measuring breathing rate must be done with the addition of a nose-plug to force the air inhalation and exhalation via the two chambers on the device. Carbon dioxide and alcohol vapor sensors are available commercially and can be incorporated into the device (e.g. MG811 and MQ-3 from Futurlec, New York, N.Y.).

To monitor the blood oxygen level for the detection of hypoxia for example, the device also contains the light detector for pulse oxymetry and CO-oximetry positioned under the upper lip 118. The red and infra-red LEDs used for oxymetry are located outside the mouth on the external side of the upper lip at the philtrum, where interference of facial hair with measurements is reduced. Because oximeter measurements monitor changes in tissue oxygenation, pulse rate is directly obtained from the oxymeter reading as well. Oximetry and CO-oximetry measurements can be made using the same light detector and three LEDs at the specific frequencies necessary for detecting tissue for monitoring hemoglobin blood concentration. This oximetry and CO-oximetry method is currently used in commercial devices for monitoring blood oxygen concentrations from the finger or the earlobe.

Blood pressure measurement has been traditionally measured by detecting Korotkoff sounds resulting from blood flow changes from modulating arterial pressure with an inflatable cuff. A combination of electrocardiography (ECG) and photoplethysmography (PPG) have recently been shown to provide a measure of blood pressure that does not require mechanical parts, as opposed to using an inflatable cuff (Y. Yoon, J. H. Cho, and G. Yoon, "Non-constrained Blood Pressure Monitoring Using ECG and PPG for Personal Healthcare," Journal of Medical Systems, vol. 33, no. 4, pp. 261-266, August 2009). The intraoral multisensor device 100 can obtain the blood pressure measurement in a way described in this publication, if ECG can be recorded from the electrodes positioned under the tongue or against the gums or lips. PPG is measured already by the oxymeter in the intraoral multisensor device 100.

Motion detection can be incorporated into the intraoral multisensor device 100 in order to monitor the patient's head movements in real time. The head motion sensor 122 can include MEMS accelerometers and gyroscopes (Invensense Corp.) that are housed with the rest of the electronics in a water-resistant box on the multisensor device 100 external to the mouth, such as in communications unit 106.

Saliva measurements can be conducted with a set of sensors positioned on the inferior aspect of the intraoral multisensor device 100 inside of the lower lip for easier consistent access to the fluid. Saliva has been shown to contain many of the same chemical markers detected in blood analysis, but in much smaller quantities (see Lima et al. 2010 for a review (D. P. Lima, D. G. Diniz, S. A. Moimaz, D. H. Sumida, and A. C. Okamoto, "Saliva: reflection of the body," Int. J. Infect. Dis., vol. 14, no. 3, p. e184-e188, March 2010). As the sensors for the particular markers become available commercially, they can be included in embodiments of the intraoral multisensor device 100. One recent example is the finding that the infrared spectrum of saliva contains diabetes-related molecular signatures (D. A. Scott, D. E. Renaud, S. Krishnasamy, P. Meric, N. Buduneli, S. Cetinkalp, and K. Z. Liu, "Diabetes-related molecular signatures in infrared spectra of human saliva," Diabetol. Metab Syndr., vol. 2, p. 48, 2010) that can be used to monitor the disease. Spectral analysis of saliva in the infrared spectrum can be attained by adding a set of LEDs, each of which are specific to a range within the spectrum of interest and monitoring the absorption by a light detector, in a way that would be similar to the oximetry sensing. Sensors technology that could be incorporated in the mouth-based device for chemical analysis of a variety of analytes are summarized in the following review: A. Bange, H. Halsall, W. Heineman, "Microfluidic immunosensor systems", Biosensors and Bioelectronics, 2005, the entire content of which is incorporated herein by reference.

Blood glucose levels could be monitored via dielectric properties of the gums and lips in the low (1-200 kHz), high (0.1-100 MHz) and microwave (1 and 2 GHz) ranges (A. Caduff, M. Mueller, A. Megej, F. Dewarrat, R. Suri, J. Klisic, M. Donath, P. Zakharov, D Schaub, W. Stahel, M. Talary, "Characteristics of a multisensory system for non invasive glucose monitoring with external validation and prospective evaluation", Biosensors and Bioelectronics, 2011, the entire content of which is incorporated herein by reference).

While the communication with the patient may be limited while the intraoral multisensor device 100 is collecting data, it may be possible to extend the communication from the patient by adding electrodes to the inside of the mouthpiece 126 and sensing the position of the tongue as the patient can touch various electrodes along the teeth. The position of the tongue can be detected by reading the impedance of each electrode, since the electrode that is being touched by the tongue will have significantly reduced impedance between the sensing electrode and a large return electrode positioned next to the interior side of either the upper or the lower lip.

Figure 5A:
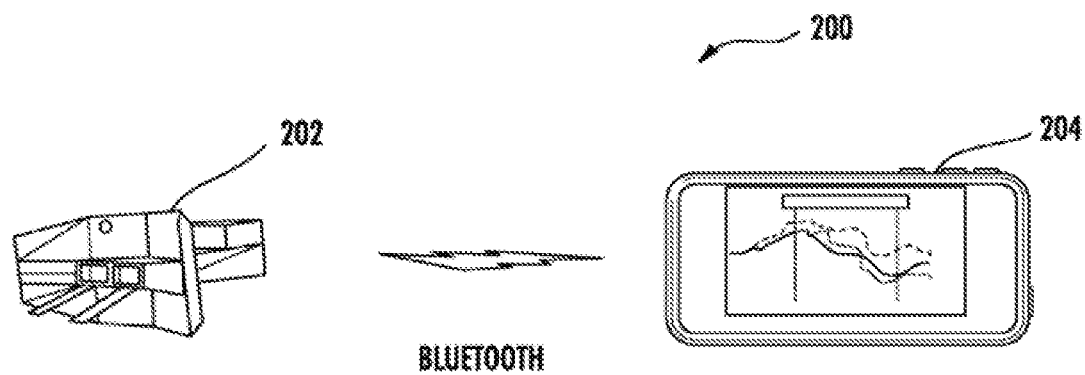
FIG. 5A is a schematic illustration of an intraoral multi-sensor system according to an embodiment of the current invention.
Figure 5B:
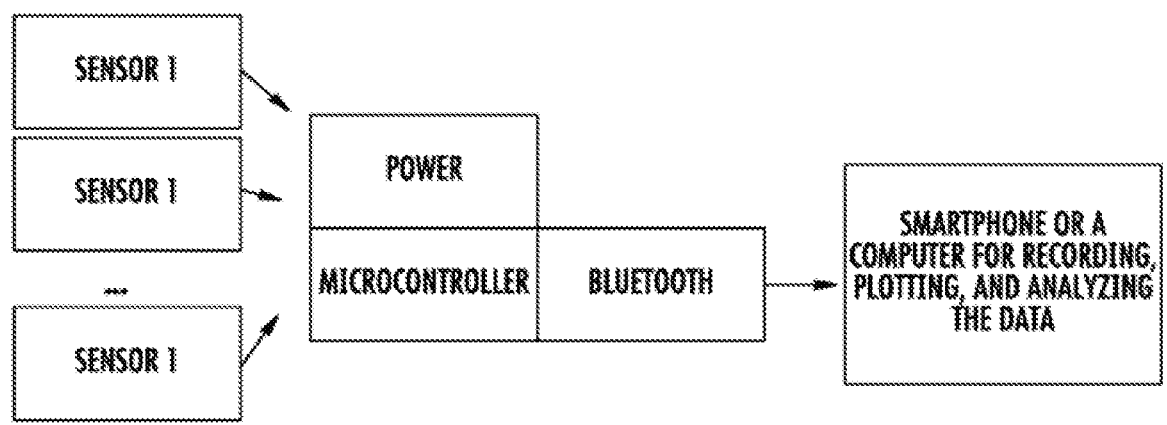
FIG. 5B is a block diagram corresponding to the intraoral multisensor system of FIG. 5A.
Figure 6:
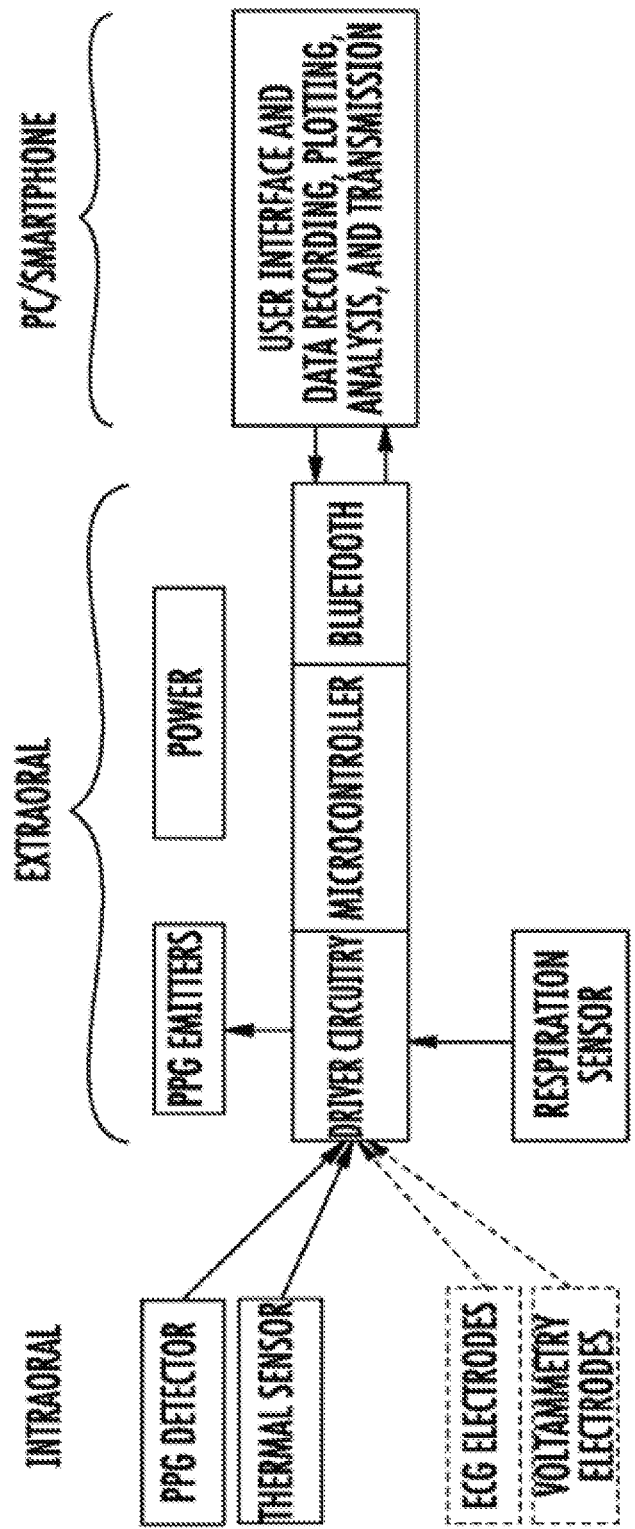
FIG. 6 is a block diagram corresponding to an intraoral multisensor system according to an embodiment of the current invention.

FIG. 5A is a schematic illustration of an intraoral multisensor system 200 according to an embodiment of the current invention. The intraoral multisensor system 200 includes an intraoral multisensor device 202 and a data processing device 204 adapted to communicate with the intraoral multisensor device 202. The intraoral multisensor device 202 can be one of the embodiments of the intraoral multisensor device 100 described above, for example. The intraoral multisensor device 202 can include a wireless transmitter configured to transmit data to the processing device 204. For example, the wireless transmitter can be, but is not limited to, a Bluetooth wireless transmitter. FIG. 5B is a block diagram schematically illustrating components of the intraoral multisensor system 200. FIG. 6 is a block diagram schematically illustrating components of the intraoral multisensor system 200 in some more detail for some particular embodiments.

The processing device 204 can be, or can include, a handheld device according to some embodiments of the current invention, such as a smart phone, a notebook or laptop computer, or a smart pad computer. The processing device 204 can also include one or more personal computer and/or network computers, including the Internet.

Figure 7A:
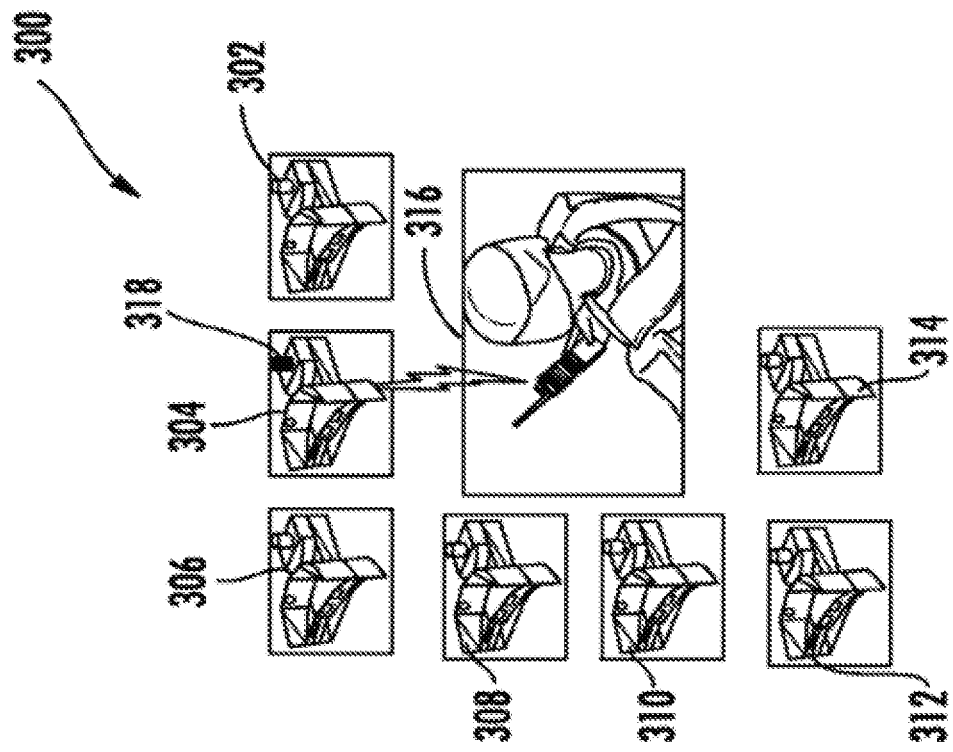
FIGS. 7A and 7B are schematic illustrations of an intraoral multisensor system according to an embodiment of the current invention.
Figure 7B:
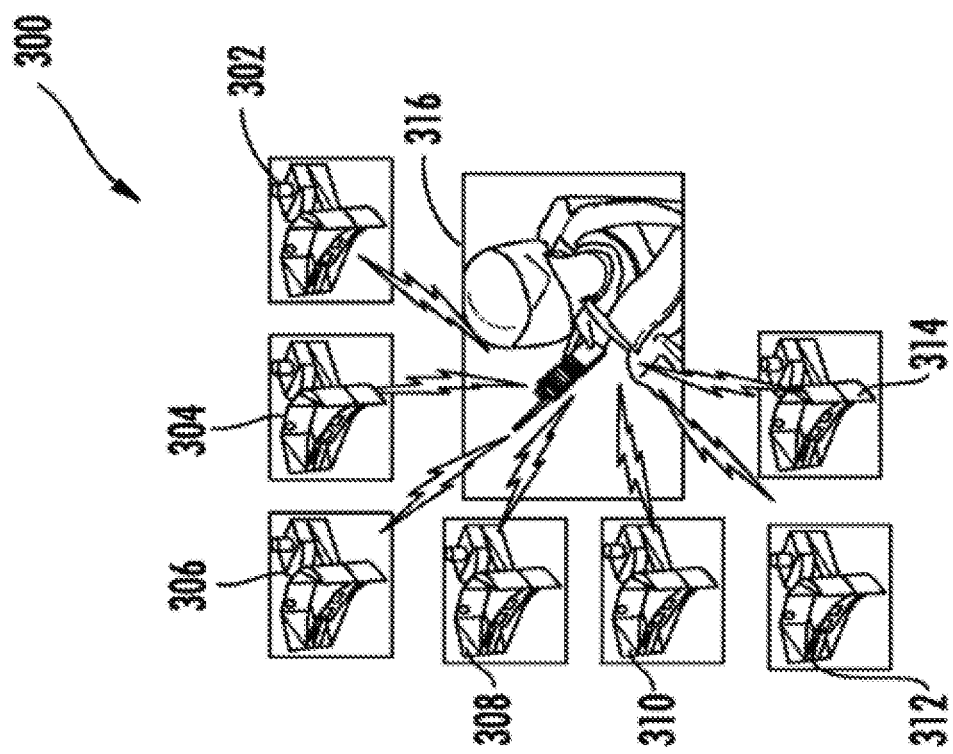

FIGS. 7A and 7B are schematic illustrations of an intraoral multisensor system 300 according to an embodiment of the current invention. The intraoral multisensor system 300 includes a plurality of intraoral multisensor devices 302-314 and a data processing device 316 adapted to communicate with the plurality of intraoral multisensor devices 302-314. Each of the plurality of intraoral multisensor devices 302-314 can be one of the embodiments of the intraoral multisensor device 100 described above, for example. The intraoral multisensor system 300 can further include a signaling component 318 configured to receive external commands to activate a signal. For example, each of the plurality of intraoral multisensor devices 302-314 can include a light, for example, in the signaling component 318 that can be activated. For example, a user could review data and select one or more patients being monitored that needs immediate assistance. Alternatively, or in addition, the data processing device 316 can be configured with software that automatically identifies one or more patients that require immediate assistance. Other embodiments could include a plurality of lights. For example, there could be multicolored lights to indicate the location and urgency of assistance needed. Alternatively, or in addition, other signaling units can be included in the signaling component 318. For example, one or more of the plurality of intraoral multisensor devices 302-314 could emit a sound, such as an alarm, a patient's heartbeat, etc. In some embodiments of the current invention, one or more of the plurality of intraoral multisensor devices 302-314 and the data processing device 316 can include a location tracking unit. For example, the location tracking unit can be a GPS device. This can be useful if the intraoral multisensor system 300 is distributed over a wide area, which could be over a fraction of a square mile up to as large as distributed around the world.

The Bluetooth communications protocol can be used to communicate the data from the intraoral multisensor device 100, 202, and/or 302-314 to a computer or a smart phone, for example. The computer in turn can forward the data via Ethernet anywhere in the world for analysis, storage, monitoring, and/or displaying the data. The communication from each intraoral multisensor device such as 302-314 can be tagged with a unique identifier. This identifier allows the computer software to monitor and record the data from several devices at the same time in the background, while viewing any one of them. This capability adds flexibility in triage situations in which limited diagnosis of many patients is needed as fast as possible. A multi-digit alphanumeric identifier can be etched on the device so that it can be identified visually and this identifier will correlate to the device identifier shown on the computer user interface screen. The identifier will be unique to the particular device and not used again. Single use identifiers will remove the confusion as to which device is being viewed at any given time.

Figure 8:
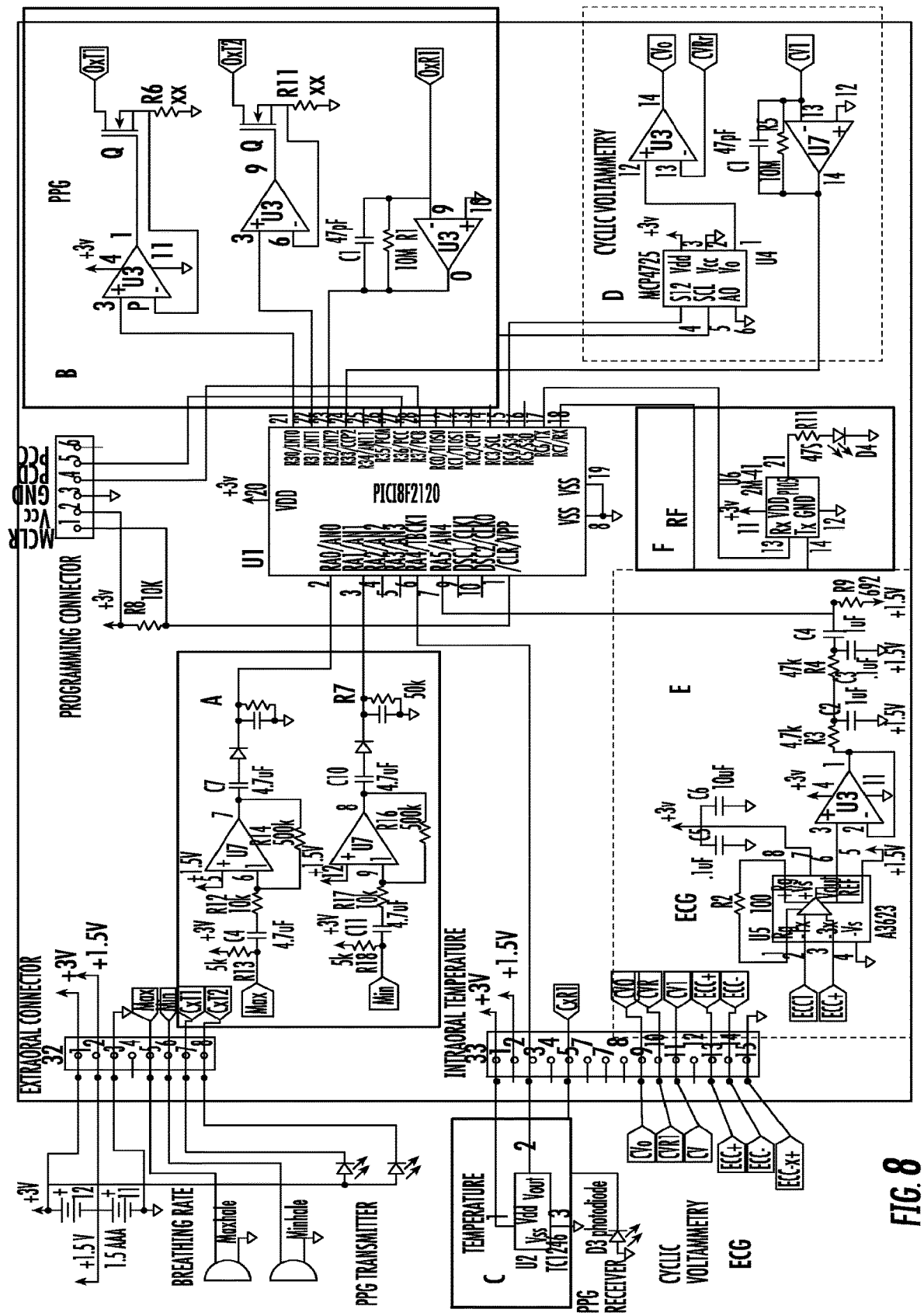
FIG. 8 is a schematic of a circuit design for a particular example according to an embodiment of the current invention. The circuitry is centered around a PIC18F2420(U1), the microcontroller that measures sensors via analog to digital converters. The thick-line boxes represent aspects of the circuit supporting the different sensors and the dashed boxes outline the circuitry for the sensors for alternative embodiments. The signals from the breathing port microphones $M_{exhale}$ and $M_{inhale}$ are amplified and filtered in (A) to detect breathing patterns and breathing rate. Photoplethysmography (PPG) monitoring via pulse-ox uses current amplifiers for each of the IR and the RED LEDs along with the current-to-voltage converter for the opto-detector are shown in (B). Temperature is detected using a TC1046 detector (C). Extensibility of the device is prototyped for saliva chemistry analysis via voltammetry (D) and the ECG monitoring circuits (E). The communication with the PC/smartphone is conducted via UART-to-Bluetooth converter RN-41, U6 (F). Access to the circuitry and power are provided via the Programming, Extraoral, and Intraoral connectors with tag labels that indicate connections to the different circuit elements.

The electronics for the intraoral multisensor devices 100, 202, and 302-314 can be designed to fit onto an extra-oral component, such as data communications unit 106 (FIG. 8). For example, a circuit board that is approximately 3.5.times.3.5 cm is suitable for some embodiments of the current invention. For example, the schematics for the electronics for an embodiment of the current invention to obtain vital measures (temperature, SpO2, pulse rate and PPG via pulse-ox, and breathing rate) for home healthcare use are shown in FIG. 8. To ensure that additional circuitry meant for other embodiments of the device will fit onto the circuit board and be able to communicate with the microprocessor, we included circuitry that can also accommodate ECG and voltammetry processing.

To control intraoral multisensor device, we chose a PIC18F2420 microprocessor from Microchip that has the appropriate bandwidth to accommodate the current embodiment with additional capability to extend to other embodiments. This microcontroller is inexpensive (~$5), confined to a small package, provides 13 channel, 10-bit analog to digital converters (A2Ds) to sample the medical sensors, and has significant bandwidth at the internally provided 40 MHz clock to help sample and process the data in real time. All 13 channels can be sampled in <300 μs (or 4300 samples per second). The communication between the microcontroller and the PC/smartphone is accomplished via a UART-to-Bluetooth converter (FIG. 8, Block F) that can communicate at up to 200 kbps. If it communicates at the standard 115 kbps, the microprocessor can transmit all 13 channels to the PC every 1.25 ms (or 800 times per second).

To examine the bandwidth of the system we look at the fastest process that the intraoral multisensor device will be recording in the near future. In the initial prototype version of the intraoral multisensor device, the fastest process (between temperature, breathing rate, and pulse-ox) is the pulse-ox PPG waveform. This process has a bandwidth of approximately 10 Hz (Reisner A, Shaltis P A, McCombie D, Asada H H (2008) Utility of the photoplethysmogram in circulatory monitoring. Anesthesiology 108: 950-958; Matviyenko S (2010) Pulse Oximeter—Standard Application Notes AN2313. In: Perform C (ed). Cypress Semiconductor, San Jose, Calif.; Webster J G (2010) Medical Instrumentation, Application and Design. John Wiley & Sons, Inc). The speed of the intraoral-multisensor-device-to-PC communication is approximately 100.times. faster than the fastest aspect of the PPG waveform, ensuring that the processor sampling rate is substantially above the 2.times. required Nyquist rate and it is capable of monitoring and transmitting all sampled data to the PC on all channels in real time.

In FIG. 8, block A of the schematic processes the microphone data from the breathing ports. The microphone signal will be greater amplitude (louder) when the air flows past the microphone than when it does not. The circuit amplifies the microphone signal and then extracts the envelope of the signal amplitude for sampling by the microcontroller. The capacitor/resistor pairs C8, R15 and C9, R7 determine the decay rate of the envelope detectors. They can be adjusted to process more refined aspects of the breathing pattern or have a more extended time constant to allow more direct monitoring of the breathing rate.

Temperature can be detected by a single component that will fit intraorally and will require power and reference to operate. It will output a voltage level that is proportional to the temperature. This voltage level is subsequently sensed by the analog-to-digital converter in the microcontroller (FIG. 8, block C). This is a low-cost self-calibrated component that is capable of sensing temperature with an accuracy of .+-.0.5.degree. C.

Figure 9:
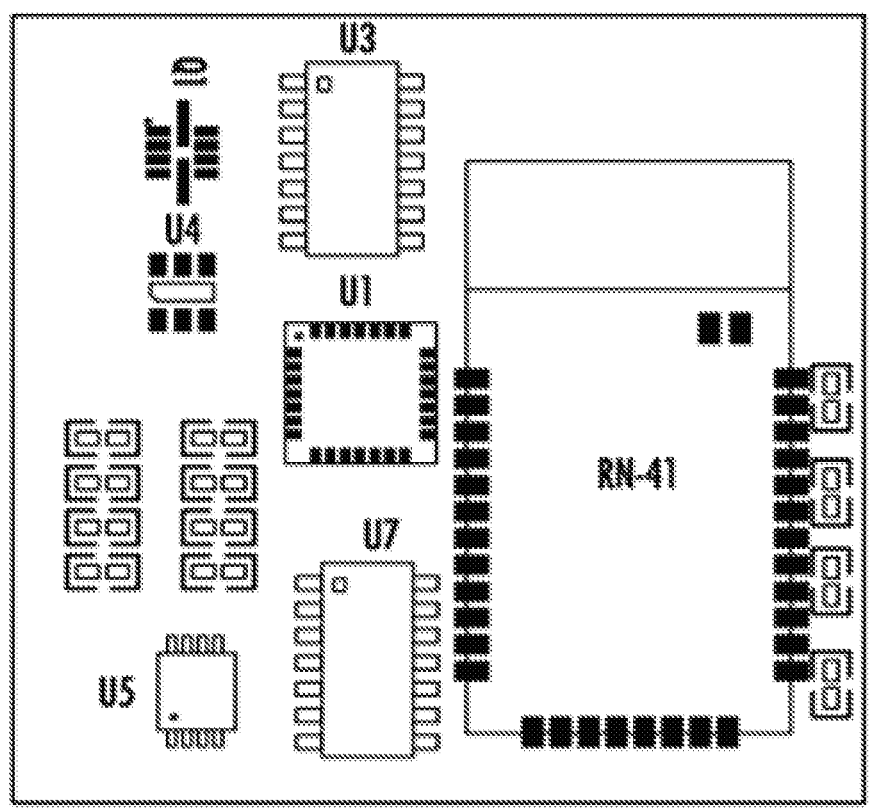
FIG. 9 shows an example of a circuit board layout corresponding to the circuit design of FIG. 8 according to an embodiment of the current invention.

Monitoring PPG and pulse-ox requires detecting the amount of light that is absorbed by the tissue from two wavelengths, one in the IR band and the other in the RED frequency band. The active current sources adjusted by R6 and R11, are used to control the precise emission from LEDs for each emission band (FIG. 8, block B). The photodetector input from OxR1 modulates the current based on the amount of incident light through the tissue from either of the LEDs. This current is measured using the active current-to-voltage converter circuit at the bottom of FIG. 8, block B. The microprocessor controls the timing of turning the IR and the RED LEDs sequentially on and off (at 200 µs/sample) and sampling of the photodetector current. The approximate layout of the circuit on a 3.5.times.3.5 cm board is shown in FIG. 9. There is sufficient room on the circuit board for the components, even accommodating the ECG and Voltammetry circuitry.

We expect that embodiments of the current invention can have a major impact on how medical diagnosis and home health care screening is conducted. Mouth-based diagnostic devices have the potential to be useful in a wide range of medical specialties in which short-duration acquisition of a large number of non-invasive measurements is required. Some examples include, but are not limited to:

Emergency medicine to allow for fast accumulation of vital information especially impacting critical triage decisions (e.g. vitals+hemoglobin and lactate levels to assess bleeding and shock+movement (EMG)).
  Respiratory care to follow chronic obstructive pulmonary disease (COPD) progression (e.g. CO2 metabolic rate and lung efficiency+exhaled gasses as predictors for lung cancer).
  Dentistry to allow for real-time analysis of periodontal disease and real time analysis of the medical health assessment of a person during periodic dental visits (e.g. vitals+saliva based inflammatory markers+cancer and heart disease markers).
  Home Healthcare to follow the progression of diabetes, hypertension, COPD, and congestive heart failure (CHF) (e.g. vitals+saliva electrolytes+glucose+CO2 metabolic rate+compliance with taking required medications). Additional benefits can include monitoring medication compliance by detecting traces of the prescribed medications in the saliva.
  Automated methods to diagnose and maintain medical care in underdeveloped countries where access to medical care is not readily available.
  Gynecology in monitoring pregnancy complications (e.g. vitals+Inflammation+illicit drug use).
  Sports medicine to monitor physical exertion (e.g. VO2max for cardiac fitness, Anaerobic threshold, Lactate, CO2 metabolic rate).

Additional benefits of some embodiments of the current invention can include real-time drug screening for use by law enforcement. Breath alcohol content tests have been used extensively to obtain real-time measurement of blood alcohol content (BAC) and can be incorporated into the present invention. While other illicit drugs are currently monitored via blood, urine, sweat, and hair testing, many can be monitored from saliva or breath vapors.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. An intraoral multisensor device, comprising:
  a mouthpiece;
  a plurality of sensors adjacent to and integrated with said mouthpiece; and
  a data communications unit configured to receive signals from said plurality of sensors,
  wherein said mouthpiece has a form to permit stable arrangement at least partially within a person's mouth such that it can remain for sensing of a plurality of biological parameters, said mouthpiece including a first intraoral portion, wherein at least one of the plurality of sensors is adjacent to and integrated with the intraoral portion and positioned within a person intraorally when the device is in use by the person, and a second extraoral portion for placement extraorally when the device is in use by the person, wherein at least one of the plurality of sensors is adjacent to and integrated with the extraoral portion and configured for use extraorally; and
  wherein the mouthpiece defines a first chamber for inhalation and a second chamber for exhalation,
  wherein one or more of said plurality of sensors is positioned within said inhalation chamber and one or more of said plurality of sensors is positioned within said exhalation chamber, wherein the first chamber is separate from the second chamber.

2. The intraoral multisensor device according to claim 1, wherein said data communications unit comprises a wireless transmitter configured to transmit data from said plurality of sensors to a processing device.

3. The intraoral multisensor device according to claim 1, wherein said plurality of sensors includes at least one of a vital signs sensor, a bite pressure sensor, a head motion sensor, a saliva analysis sensor and a tongue position sensor.

4. The intraoral multisensor device according to claim 3, wherein said plurality of vital signs sensors comprise at least two sensors selected from a temperature sensor, a blood pressure sensor, a pulse rate sensor, a breath condensate analysis, a breath pattern analysis, an EMG sensor, an EEG sensor, and an ECG sensor, and a respiratory rate sensor.

5. The intraoral multisensor device according to claim 1, wherein said first intraoral portion is attachable to and detachable from said data communications unit such that said first intraoral portion can be at least one of cleaned for reuse or discarded to be replaced with a new first intraoral portion.

6. The intraoral multisensor device according to claim 1, wherein at least one of the plurality of sensors is attached to and integrated to the mouthpiece to be positioned against a person's lip.

7. The intraoral multisensor device according to claim 1, wherein at least one of the plurality of sensors is attached to and integrated to the mouthpiece to sense one or more properties from a person's lip.

8. The intraoral multisensor device according to claim 1, wherein at least one of the plurality of sensors is attached to and integrated to the mouthpiece to obtain measurements from a person's tongue.

9. An intraoral multisensor system, comprising:
  an intraoral multisensor device; and
  a data processing device adapted to communicate with said intraoral multisensor device,
  wherein said intraoral multisensor device comprises:
    a mouthpiece, said mouthpiece including a first intraoral portion and a second extraoral portion extraorally when the device is in use by the person;
    a first plurality of sensors adjacent to and integrated with said mouthpiece, the first plurality of sensors being adjacent to and integrated with the first intraoral portion of the mouthpiece and positioned within a person intraorally when the device is in use by the person to sense one or more properties internal to the person and a second plurality of sensors being adjacent to and integrated with the second extraoral portion of the mouthpiece and positioned extraorally when the device is in use by the person to sense one or more properties external to a person;

a first inhalation sensor chamber and a second exhalation sensor chamber separate from the second exhalation sensor chamber positioned within said mouthpiece, and at least one of said plurality of sensors positioned within said first inhalation sensor chamber and at least one of said plurality of sensors positioned within said second exhalation sensor chamber, wherein intraoral and extraoral environments are in fluid communication via said first inhalation and second exhalation sensor chambers; and a data communications unit configured to receive signals from said plurality of sensors and transmit data from the data communications unit.

10. The intraoral multisensor system according to claim 9, further comprising a plurality of intraoral multisensor devices, wherein said data processing device is further adapted to communicate with each of said plurality of intraoral multisensor devices.

11. The intraoral multisensor system according to claim 10, further comprising a display unit adapted to communicate with said data processing unit to display information received from at least one of said plurality of intraoral multisensor devices.

12. The intraoral multisensor system according to claim 9, wherein said data communications unit comprises a wireless transmitter configured to transmit data from said plurality of sensors to said data processing device.

13. The intraoral multisensor system according to claim 9, wherein said data communications unit comprises a user interface to at least one of output information directly to a user or receive user input information.

14. The intraoral multisensor system according to claim 9, wherein said first plurality of sensors and said second plurality of sensors include at least one of a vital signs sensor, a blood oxygen level sensor, a bite pressure sensor, a head motion sensor, a saliva analysis sensor, a tongue position sensor, or a breath pattern analyzer.

15. The intraoral multisensor system according to claim 14, wherein said plurality of vital signs sensors comprise at least two sensors selected from a temperature sensor, a blood pressure sensor, a pulse rate sensor, a breath condensate analysis, a breath pattern analysis, an EMG sensor, an EEG sensor, and an ECG sensor, and a respiratory rate sensor.

16. The intraoral multisensor system according to claim 9, wherein said first intraoral portion is attachable to and detachable from said data communications unit such that said first intraoral portion can be at least one of cleaned for reuse or discarded to be replaced with a new first intraoral portion.

17. The intraoral multisensor system according to claim 9, further comprising a signaling component configured to receive external commands to activate a signal.

18. The intraoral multisensor system according to claim 17, wherein said signal is at least one of a visual or audio signal.

19. The intraoral multisensor system according to claim 9, further comprising a location tracking unit.

20. The intraoral multisensor system according to claim 9, wherein said mouthpiece has a form to permit stable arrangement at least partially within a person's mouth such that it can remain for hands-free sensing of a plurality of biological parameters and to provide data for said plurality of biological parameters to said data processing device.

21. The intraoral multisensor device according to claim 9, wherein the at least one of the plurality of sensors is configured to sense one or more of blood flow and electrocardiogram from the person's lip.

22. An intraoral multisensor system, comprising:
an intraoral multisensor device having a body; and
a data processing device incorporated into said body and adapted to communicate with said intraoral multisensor device,
wherein said intraoral multisensor device comprises:
  a mouthpiece, said mouthpiece including a first intraoral portion and a second extraoral portion;
  a plurality of sensors adjacent to and integrated with said mouthpiece, at least one of the plurality of sensors being adjacent to and integrated with the mouthpiece and positioned within a person intraorally when the device is in use by the person to sense one or more properties from both internal to and external to a person; and
  a first inhalation sensor chamber and a second exhalation sensor chamber separate from said first inhalation sensor chamber positioned within said mouthpiece;
  wherein intraoral and extraoral environments are in fluid communication via said first and second exhalation sensor chambers, wherein the first inhalation sensor chamber includes a first one-way valve and the second exhalation sensor chamber includes a second one-way valve, the first one-way valve being oriented opposite the second one-way valve, wherein a first sensor of said plurality of sensors is positioned within the first inhalation sensor chamber and a second sensor of said plurality of sensors is positioned within said second exhalation sensor chamber, wherein said first sensor is in said first inhalation sensor chamber and upstream of said first one-way valve and said second sensor is in said second exhalation sensor chamber and upstream of said second one-way valve;
a data communications unit incorporated into the body and separable from said mouthpiece configured to receive signals from said plurality of sensors and transmit data from the data communications unit.

23. The intraoral multisensor system according to claim 22, wherein said first sensor of said plurality of sensors and said second sensor of said plurality of sensors is an alcohol sensor.

24. The intraoral multisensor system according to claim 22, wherein said first sensor of said plurality of sensors and said second sensor of said plurality of sensors are positioned within said second extraoral portion.

25. The intraoral multisensor system according to claim 22, wherein said mouthpiece is detachable from said body.

26. The intraoral multisensor system according to claim 22, wherein said first sensor is a microphone and said second sensor includes an alcohol sensor or carbon dioxide sensor.

* * * * *